United States Patent
Tee, Jr. et al.

(10) Patent No.: US 8,513,483 B2
(45) Date of Patent: *Aug. 20, 2013

(54) HYDROPHOBIC SURFACE COATED MATERIAL FOR USE IN ABSORBENT ARTICLES

(75) Inventors: Johannson Jimmy Tee, Jr., Mason, OH (US); Kemal Vatansever Catalan, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 265 days.

This patent is subject to a terminal disclaimer.

(21) Appl. No.: 12/691,929

(22) Filed: Jan. 22, 2010

(65) Prior Publication Data

US 2010/0222757 A1    Sep. 2, 2010

Related U.S. Application Data

(60) Provisional application No. 61/156,090, filed on Feb. 27, 2009.

(51) Int. Cl.
*A61F 13/15*    (2006.01)

(52) U.S. Cl.
USPC .................... 604/381; 604/378; 604/385.28

(58) Field of Classification Search
USPC .................... 604/381, 378, 385.28
See application file for complete search history.

(56) References Cited

U.S. PATENT DOCUMENTS

| | | |
|---|---|---|
| 3,860,003 A | 1/1975 | Buell |
| 4,610,678 A | 9/1986 | Weisman et al. |
| 4,673,402 A | 6/1987 | Weisman et al. |
| 4,695,278 A | 9/1987 | Lawson |
| 4,795,454 A | 1/1989 | Dragoo |
| 4,808,178 A | 2/1989 | Aziz et al. |
| 4,834,735 A | 5/1989 | Alemany et al. |
| 4,888,231 A | 12/1989 | Angstadt |
| 4,909,803 A | 3/1990 | Aziz et al. |
| 5,147,345 A | 9/1992 | Young et al. |
| 5,234,423 A | 8/1993 | Alemany et al. |
| 6,120,487 A | 9/2000 | Ashton |
| 6,482,191 B1 | 11/2002 | Roe et al. |
| 2005/0177123 A1 | 8/2005 | Catalan |
| 2005/0234411 A1 | 10/2005 | Ashton et al. |
| 2006/0189956 A1 | 8/2006 | Catalan |
| 2008/0004591 A1 | 1/2008 | Desai et al. |

*Primary Examiner* — Jacqueline F. Stephens
(74) *Attorney, Agent, or Firm* — Kathleen Y. Carter; John G. Powell

(57) ABSTRACT

An improved barrier member for an absorbent article that includes a nonwoven treated with a hydrophobic surface coating. The hydrophobic surface coating includes a non-aqueous, solventless, multicomponent silicone composition. The hydrophobic surface coating may be substantially free of aminosilicones.

18 Claims, 8 Drawing Sheets

HYDROPHOBIC SURFACE COATED MATERIAL FOR USE IN ABSORBENT ARTICLES

CROSS REFERENCE TO RELATED APPLICATIONS

This application claims the benefit of U.S. Provisional Application No. 61/156,090, filed Feb. 27, 2009.

FIELD OF THE INVENTION

Disclosed are hydrophobic surface coated materials and absorbent articles that include such materials. Specifically, there is disclosed lightweight nonwoven materials and lightweight nonwoven laminate materials treated with a hydrophobic surface coating to improve the barrier properties of absorbent article components that include such lightweight materials.

BACKGROUND OF THE INVENTION

Disposable absorbent articles (e.g., diapers, training pants, pant-like articles, feminine hygiene products, and adult incontinence articles) are commonly used to absorb and contain body exudates. Such articles are typically used to prevent body exudates from soiling, wetting, or otherwise contaminating clothing or other articles such as bedding that may come into contact with the absorbent article. However, it is known that, in at least some instances, bodily exudates may escape the boundaries of an absorbent article due to, for example, leakage from gaps between the article and the wearer's skin and/or from seepage through the material that makes up the absorbent article. Seepage may be caused by the inability of one or more the materials used in the construction of the absorbent article or absorbent article component to provide an effective barrier to such bodily fluids. For example, with sufficient pressure or loading, urine may penetrate through absorbent article components or component portions, which are intended to prevent the passage of urine (e.g., the leg cuff or outer cover of a diaper). Additionally, loose fecal matter that is not easily absorbed by the absorbent article may remain on top of the article's liquid receiving member (e.g., topsheet). During the course of wearing the article, fecal matter may spread over the liquid receiving member and may even leak from the article.

Traditional absorbent articles such as diapers typically include one or more barrier members (e.g., barrier leg cuffs, gasketing cuffs, secondary topsheets, core covers, outer covers, and portions of these). Other features such as pockets, spacers, transverse barriers, apertured topsheets and the like may be included to isolate, immobilize, and/or confine body exudates such as fecal matter. Attempts have been made at improving the barrier characteristics of absorbent article components and/or component portions by selecting barrier member material(s) and/or combinations of material that provide a particular benefit. For example, an absorbent article component may be made substantially liquid impervious through the use of polymeric films, but such films may also be vapor and air impervious Thus, even though the article may have suitable barrier properties, it may occlude the skin of the wearer, resulting in diaper rash and/or other undesirable effects. The use of nonwoven materials is common in absorbent articles since they typically provide vapor and air perviousness (i.e., they are "breathable"), but nonwovens may not provide suitable imperviousness to liquids in at least some instances.

One way to improve the liquid imperviousness of nonwovens is to increase the basis weight of the nonwoven, since nonwovens with higher basis weights are known to have improved liquid imperviousness. Another way to improve the liquid imperviousness of a nonwoven is through the use of multiple layers of material configured in a laminate structure (e.g., a commonly known spunbond-meltblown-spunbond ("SMS") tri-laminate structure). In an SMS laminate, the meltblown layer typically provides the desired liquid imperviousness, but generally exhibits undesirable abrasion resistance and strength. The spunbond layers of the SMS laminate are typically included to provide the desired abrasion resistance and strength to the laminate. Increased basis weight materials and laminate structures may provide a degree of liquid imperviousness and maintain some vapor perviousness, but the increased amount and/or layers of material may result in undesirable stiffness of the material, increased cost of material manufacture, and increased disposal volume.

Another way to improve the liquid imperviousness of a nonwoven to liquids such as urine, menses, and loose fecal matter is to treat the nonwoven with a composition that renders the nonwoven, or portions thereof, more hydrophobic, for example, by coating the nonwoven with a composition containing one or more silicone polymers. Examples of surface coatings for improving the barrier properties of a nonwoven are disclosed in U.S. Publication Nos. 2005/0177123 and 2006/0189956. Known silicone containing coatings are typically formed as hydrophilic solutions (e.g., an emulsion of a polar liquid component such as water, a non-polar liquid component such as silicone oil, and other optional ingredient(s) such as surfactant(s) and stabilizer(s)). The active hydrophobic component in such solutions (e.g., a silicone composition) is typically present as a relatively small weight percentage of the solution (e.g., less than 50%, 40%, or even 20%), based on the total weight of the solution. Thus, in order to provide the desired amount of the active hydrophobic component per unit area of nonwoven substrate, it may be necessary to apply a relatively large amount of an aqueous solution to the nonwoven, and since the aqueous component of such solutions is typically removed from the substrate (e.g., by drying), the cost, amount of waste, and/or process complexity associated with removing the aqueous component may be undesirably increased. Further, in at least some instances, nonwovens are formed from hydrophobic materials (e.g., polyolefin fibers), and applying an aqueous solution to the hydrophobic nonwoven may cause the solution to undesirably spread across the substrate resulting in a non-uniform or random distribution of the active ingredient. The relatively non-uniform distribution of the active hydrophobic component may result in one or more portions of the material being substantially untreated and therefore subject to an increased potential for liquid to undesirably pass through the substrate or a portion thereof. Still further, aqueous solutions typically include additional ingredients such as surfactants and other additives to stabilize the solution. Surfactants are known to reduce the interfacial tension between liquids having different surface tensions and facilitate the spreading of the composition. When exposed to bodily fluids such as urine, surfactants and/or other ingredients in aqueous solutions may be transported away from their intended location (e.g., they may migrate to the absorbent core and/or some other absorbent article component). The migration of the surfactants and/or other ingredients from their intended location may undesirably impact the barrier properties of the portion of the absorbent article that the surfactant and/or other ingredients are migrating from, as well as the portion of the absorbent article that the surfactant and/or other ingredients are migrating to.

Accordingly, it would be desirable to provide an absorbent article that includes a material with improved barrier properties. It would further be desirable to provide a material, which includes a hydrophobic surface coating that is substantially uniformly distributed across the material. It would further be desirable to provide a material, which includes a hydrophobic surface coating that exhibits reduced migration of mobile components.

SUMMARY OF THE INVENTION

In order provide a solution to the problems described above, disclosed herein is an absorbent article that includes a liquid pervious first topsheet. The first topsheet has an interior surface and an exterior surface. The absorbent article also includes an outer cover having an interior surface and an exterior surface. The outer cover is at least partially joined to the topsheet. The absorbent article further includes an absorbent core disposed between the topsheet and the outer cover. The absorbent article also includes a barrier member selected from the group consisting of a core cover, an outer cover, a gasketing cuff, a barrier cuff, an elasticized topsheet, and combinations of these. The barrier member has an interior and an exterior surface, and includes a nonwoven. The absorbent article further includes a hydrophobic surface coating disposed on at least one surface of the nonwoven. The hydrophobic surface coating includes a non-aqueous, solventless, multicomponent silicone composition. The silicone composition includes at least one silicone polymer and is substantially free of aminosilicones.

DETAILED DESCRIPTION OF THE INVENTION

Definitions

Figure 1:
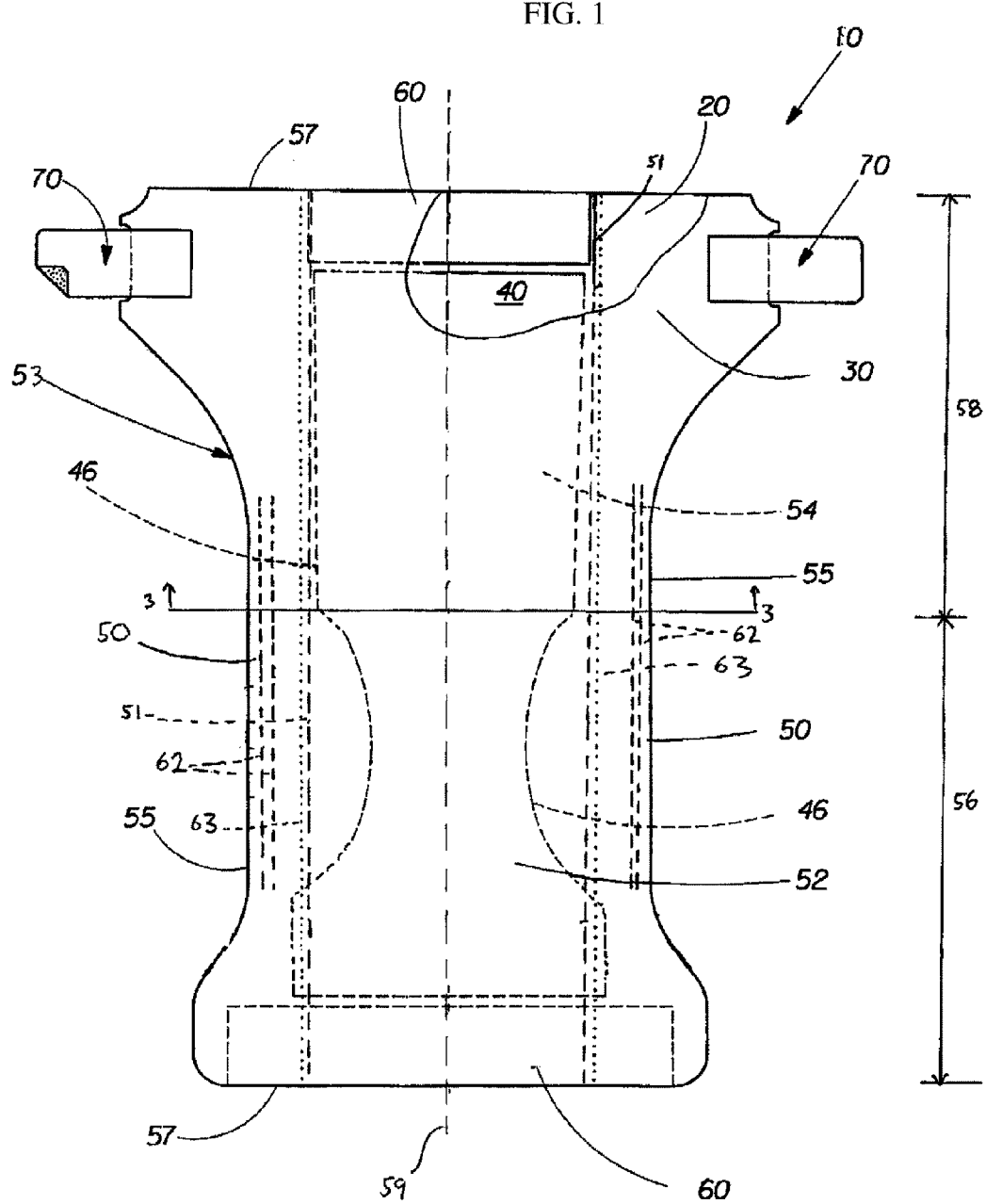
FIG. 1 shows a plan view of an exemplary absorbent article.

"Absorbent articles" are devices that absorb and contain body exudates and which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as the diaper illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Body-facing surface" means a surface of the article or component which is intended to be worn toward or adjacent to the body of a wearer.

"Disposable" means articles that are generally not intended to be laundered or otherwise restored or reused. (i.e., they are intended to be discarded after a single use and, preferably, to be recycled, composted or otherwise discarded in an environmentally compatible manner).

"Disposed" means the placement of one element of an article relative to another element of an article. For example, the elements may be formed (joined and positioned) in a particular place or position as a unitary structure with other elements of the diaper or as a separate element joined to another element of the diaper.

"Flexible" means materials which are compliant and that readily conform to the general shape and contours of a human body.

"Garment-facing surface" means a surface of the article or component which is on the opposite side of the body-facing surface and is intended to be worn toward or placed adjacent to the wearer's undergarments or clothing when the absorbent article is worn.

"Hydrophilic" means having a contact angle of less than 90° according to The American Chemical Society Publication "Contact Angle, Wettability, and Adhesion," edited by Robert F. Gould and copyrighted in 1964.

"Hydrophobic" means having a contact angle greater than or equal to 90° according to The American Chemical Society Publication "Contact Angle, Wettability, and Adhesion," edited by Robert F. Gould and copyrighted in 1964. In certain embodiments, hydrophobic surfaces may exhibit contact angles >120°, >140°, or even >150°. Hydrophobic liquid compositions (e.g., the HSC compositions disclosed herein) are generally immiscible in water.

"Hydrophobic surface coating" or "HSC" means a composition that has been applied to a surface in order to render the surface hydrophobic or more hydrophobic. "Hydrophobic surface coating composition" means a composition that is to be applied to a surface in order to provide a hydrophobic surface coating.

"Joined" means configurations whereby an element is directly secured to another element by affixing the element directly to the other element and to configurations whereby an element is indirectly secured to another element by affixing the element to intermediate member(s), which in turn are affixed to the other element.

"Laminated structure" or "laminate" means a structure in which one layer, material, component, web, or substrate is joined, at least in part, to another layer, material, component, web, or substrate. As stated elsewhere in this application, a layer, material, component, web, or substrate may be folded over and bonded to itself to form a laminate.

"Low surface tension fluids" means fluids having a surface tension of less than 72 dynes/cm, 60 dynes/cm, or even less than 60 dynes/cm. For example, from 25 to 55 dynes/cm when measured according to the Interfacial Tension Measurement method below.

"Multicomponent," when referring to silicone compositions, means a silicone composition that includes two or more chemically distinct silicone polymers.

"Non-aqueous" means a composition contains little (i.e., less than one weight % by weight of the composition) or no (zero weight %) water.

"Nonwoven" means a manufactured sheet, web, or batt of directionally or randomly oriented fibers, bonded by friction, and/or cohesion, excluding paper and products which are woven, knitted, tufted, stitchbonded, incorporating binding yarns or filament, or felted by wet milling, whether or not additionally needled. The fibers may be of natural or manmade origin. The fibers may be staple or continuous filaments or be formed in situ. The porous, fibrous structure of a nonwoven may be configured to be liquid pervious or impervious, as desired.

"Solventless" means the absence of a liquid medium such as water or an organic solvent for carrying the active component(s) of an HSC composition. At least some conventional, non-aqueous surface coatings include organic solvents (e.g., toluene, ethanol, hexane, acetone, methyl acetate, petrol ether, and turpentine), which need to be removed, for example, through evaporation. It is to be understood that even after the evaporation of the solvent such surface coating compositions are still not solventless surface coatings as contemplated herein. Similarly, conventional aqueous surface coatings include more than 1% water by weight of the composition, which is typically removed, for example, through drying.

"Telomer" means an addition polymer, typically of low molecular weight, in which the growth of molecules is terminated by a radical-supplying chain transfer agent or a low molecular weight polymer in which the terminal group on the end of the chain-like molecule is not the same as the side group. "Oligomer" means a polymer comprising relatively few (i.e., two to ten) repeating units.

"Web" means a material capable of being wound into a roll. Webs may be films, nonwovens, laminates, apertured laminates, etc. The face of a web refers to one of its large two dimensional surfaces, as opposed to its edge.

While one or more portions of the present disclosure may refer to a disposable diaper, it is to be understood that the invention is not limited to such embodiments, but may in fact be practiced to great advantage with any suitable absorbent article. Further, it is easily foreseeable that multicomponent, non-aqueous, solventless HSCs as described herein may have applications as release liners for pressure sensitive adhesive laminates & tapes, paper machine applications, casting papers, food-grade release and packaging papers and well as general purpose packaging.

Absorbent Article

FIG. 1 is a plan view of a diaper 10 in a flat-out, uncontracted state (i.e., with no elastic induced contraction). Portions of FIG. 1 are cut away to more clearly show the construction of the diaper 10. The garment-facing surface 52 of the diaper 10 is oriented towards the viewer and the opposing wearer-facing surface 54 is oriented away from the viewer. As shown in FIG. 1, the diaper 10 may include a liquid pervious topsheet 20; a liquid impervious outer cover 30 joined with the topsheet 20; and an absorbent core assembly 40 positioned between the topsheet 20 and the outer cover 30. The diaper 10 may further include one or more gasketing cuffs 50 and/or barrier cuffs 51. The diaper 10 may include an elastic waist feature 60 and a fastening system 70. The diaper 10 may include a first waist region 56, a second waist region 58, and a periphery 53 which is defined by the longitudinal side edges 55 and end edges 57. The inner, wearer-facing surface 54 of the diaper 10 may include at least a portion of the topsheet 20 and other components, which may be joined to the topsheet 20. The outer, garment-facing surface 52 may include at least a portion of the outer cover 30 and other components, which may be joined to the outer cover 30.

The topsheet 20 may be flexible, soft feeling, and non-irritating to the wearer's skin. It may be desirable to configure the topsheet to be liquid pervious (i.e., permitting liquids such as menses, urine, and/or runny feces to readily penetrate through its thickness). For example, the topsheet 20 may be made of a hydrophilic material that promotes rapid transfer of liquids through the topsheet 20. In certain embodiments, the topsheet 20 may be made of a hydrophobic material (e.g., polyolefin nonwoven and/or film), at least a portion of which (e.g., the wearer-facing surface) has been treated to be hydrophilic so that liquids will transfer through the topsheet more rapidly. The topsheet 20 or portions thereof may be rendered more hydrophilic, for example, by treatment with a surfactant. A suitable topsheet 20 may be manufactured from a wide range of materials such as woven and nonwoven materials (e.g., a nonwoven web of fibers); polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers. In certain embodiments, the topsheet 20 may comprise a nonwoven (e.g., a lightweight nonwoven laminate having a total basis weight of less than 15 grams per square meter ("gsm")) with an HSC, as described in greater detail below. In certain embodiments, an absorbent article may include one or more topsheets 20 and/or topsheet layers (e.g., a second topsheet) that include a lightweight nonwoven laminate with an HSC.

The absorbent core assembly 40 is generally capable of absorbing and retaining liquids (e.g., menses, urine, and/or other bodily exudates). The absorbent core assembly 40 may be compressible, conformable, and non-irritating to the wearer's skin. The configuration and construction of the absorbent core assembly 40 may be varied (e.g., the absorbent core assembly may have varying caliper zones and/or have a profile so as to be thicker in the center; hydrophilic gradients; superabsorbent gradients; lower average density and lower average basis weight zones (e.g., acquisition zones); and/or may comprise one or more layers or structures). The size and absorbent capacity of the absorbent core assembly 40 may be varied to accommodate different uses such as diapers, incontinence pads, pantiliners, regular sanitary napkins, and overnight sanitary napkins, and to accommodate wearers ranging from infants to adults. In certain embodiments, the diaper 10 may have an asymmetric, modified T-shaped absorbent core assembly 40 having a narrowing of the side edge 46 in the first waist region 56 but remaining generally rectangular-shaped in the second waist region 58. In certain embodiments, the absorbent core may be arranged in a bucket-type configuration, for example, as described in U.S. Publication No. 2008/0004591, titled "Absorbent Article Having An Anchored Core Assembly," filed by Desai, et al., Jun. 7, 2007. Other suitable examples of absorbent core assemblies are described in U.S. Pat. Nos. 4,610,678, 4,673,402, 4,888,231, and 4,834,735. The absorbent core assembly may further comprise a dual core system containing an acquisition/distribution core of chemically stiffened fibers positioned over an absorbent storage core, as detailed in U.S. Pat. Nos. 5,234,423 and 5,147,345. The absorbent core assembly 40 may include absorbent components that are commonly used in absorbent articles, for example, a dusting layer, a wicking or acquisition layer, and/or a secondary topsheet for increasing the wearer's comfort.

As shown in FIG. 1, the outer cover 30 may be configured to substantially cover the entire exterior, garment facing surface 52 of the diaper 10. The absorbent core assembly 40 may be joined with the topsheet 20, the outer cover 30, or both in any suitable manner known in the art by any suitable attachment means known in the art. For example, the outer cover 30 and/or the first topsheet 20 may be secured to the absorbent core assembly 40 or to each other by a uniform continuous layer of adhesive, a patterned layer of adhesive, or an array of separate lines, spirals, or spots of adhesive, heat bonds, pressure bonds, ultrasonic bonds, dynamic mechanical bonds, or any other suitable attachment means or combinations of these attachment means as are known in the art. The outer cover 30 may be manufactured from a thin plastic film, although other flexible liquid impervious materials may also be used. The outer cover 30 may comprise a woven or nonwoven material, polymeric films such as thermoplastic films of polyethylene or polypropylene, and/or composite materials such as a film-coated nonwoven material or a film-nonwoven laminate. An example of a suitable outer cover 30 is a polyethylene film having a thickness of from about 0.012 mm (0.5 mils) to about 0.051 mm (2.0 mils). Exemplary polyethylene films are manufactured by Clopay Corporation of Cincinnati, Ohio, under the designation P18-1401 and by Tredegar Film Products of Terre Haute, Ind., under the designation XP-39385. In certain embodiments, the outer cover 30 may include two or more layers of material joined together to form a laminate structure. For example, the outer cover 30 may include one or more liquid impervious film layers 31 joined to one or more nonwoven layers 32 in any suitable configuration desired. In certain embodiments, the outer cover 30 may be used to improve the aesthetic and/or textural quality of the exterior surface of the diaper 10. For example, it may be desirable to provide an outer cover 30 with an embossed or matte finish, which imparts a cloth-like appearance and/or feel to the outer cover 30.

The outer cover 30 may be impervious to liquids (e.g., low surface tension fluids such as menses, urine, and/or runny feces) to help prevent bodily exudates absorbed and contained in the absorbent core assembly 40 from wetting articles that contact the absorbent article (e.g., bedsheets, pants, pajamas and undergarments). Further, the outer cover 30 may permit vapors to escape from the absorbent core assembly 40 while still preventing the passage of exudates (i.e., the outer cover may be breathable). The size of the outer cover 30 is generally dictated by the size of the absorbent core assembly 40 and the exact absorbent article design selected. However, in certain embodiments, the outer cover 30 may be constructed to provide increased barrier protection. In certain embodiments, the outer cover 30 may include a nonwoven (e.g., a lightweight nonwoven laminate material) with an HSC. Use of a nonwoven, and in particular a lightweight nonwoven laminate material, in combination with a hydrophobic surface-coating is believed to provide the desirable aesthetic benefits of a cloth-like look and feel while also providing increased barrier protection with a lower basis weight and lower cost material.

Barrier Member

In a certain embodiments, the diaper 10 may further include at least one barrier member. Barrier members are physical structures joined or applied to the diaper 10 to improve the barrier properties of the diaper 10. Barrier members include, but are not limited to, absorbent article components such as a core cover, an outer cover, a barrier cuff, a gasketing cuff, and an elasticized topsheet. It may be desirable that the barrier member include a lightweight nonwoven laminate with an HSC disposed thereon.

The diaper 10 may include one or more gasketing cuffs 50 for providing improved containment of liquids and other body exudates, especially around the leg openings of the diaper 10. Gasketing cuffs 50 may also be referred to as leg cuffs, outer leg cuffs, leg bands, side flaps, or elastic cuffs. U.S. Pat. No. 3,860,003 describes a disposable diaper that includes a contractible leg opening having a side flap and one or more elastic members to provide an elasticized leg cuff. Elasticity may be imparted to the gasketing cuff 50 by one or more elastic members 62. In certain embodiments, the diaper 10 may include one or more barrier cuffs 51 which also provide improved containment of liquids and other body exudates. Barrier cuffs 51 may also be referred to as barrier leg cuffs, inner leg cuffs, or "stand-up" elasticized flaps. U.S. Pat. Nos. 4,808,178 and 4,909,803 issued to Aziz et al. on Feb. 28, 1989 and Mar. 20, 1990, respectively, describe disposable diapers having "stand-up" elasticized flaps that improve the containment of the leg regions. As with gasketing cuffs 50, barrier cuffs 51 may also include one or more elastic members 63. The Elastic member 63 may provide elasticity to the barrier cuff 51 which may aid in keeping the barrier cuff 51 in a "stand-up" position. The gasketing cuff 50 and the barrier cuff 51 may both be provided by way of an integral cuff, as exemplified in U.S. Pat. Nos. 4,695,278 and 4,795,454 issued to Lawson on Sep. 22, 1987 and to Dragoo on Jan. 3, 1989, respectively. Additional cuffs may be provided as detailed in U.S. Statutory Invention Registration H1630, which published Jan. 7, 1997.

Figure 2:
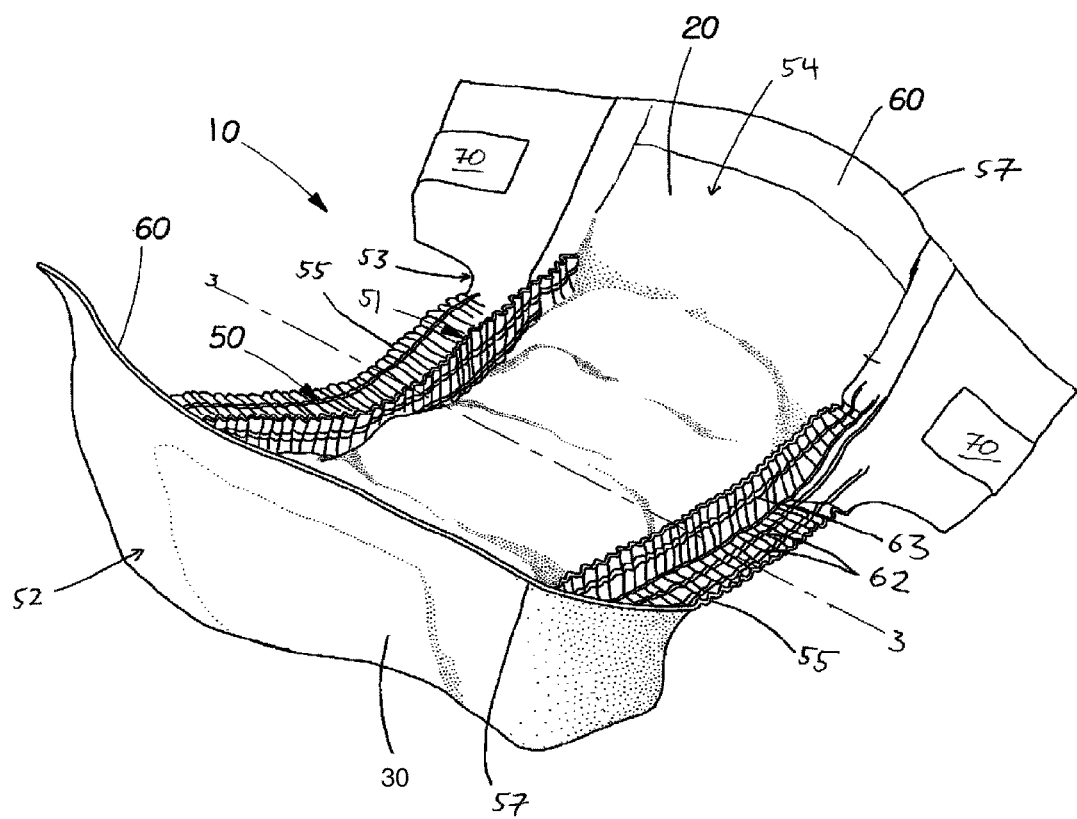
FIG. 2 shows a perspective view of an exemplary absorbent article.

FIG. 2 is a perspective view of the diaper 10 of FIG. 1 in a partially contracted state (i.e., with at least some elastic induced contraction).

Figure 3A:
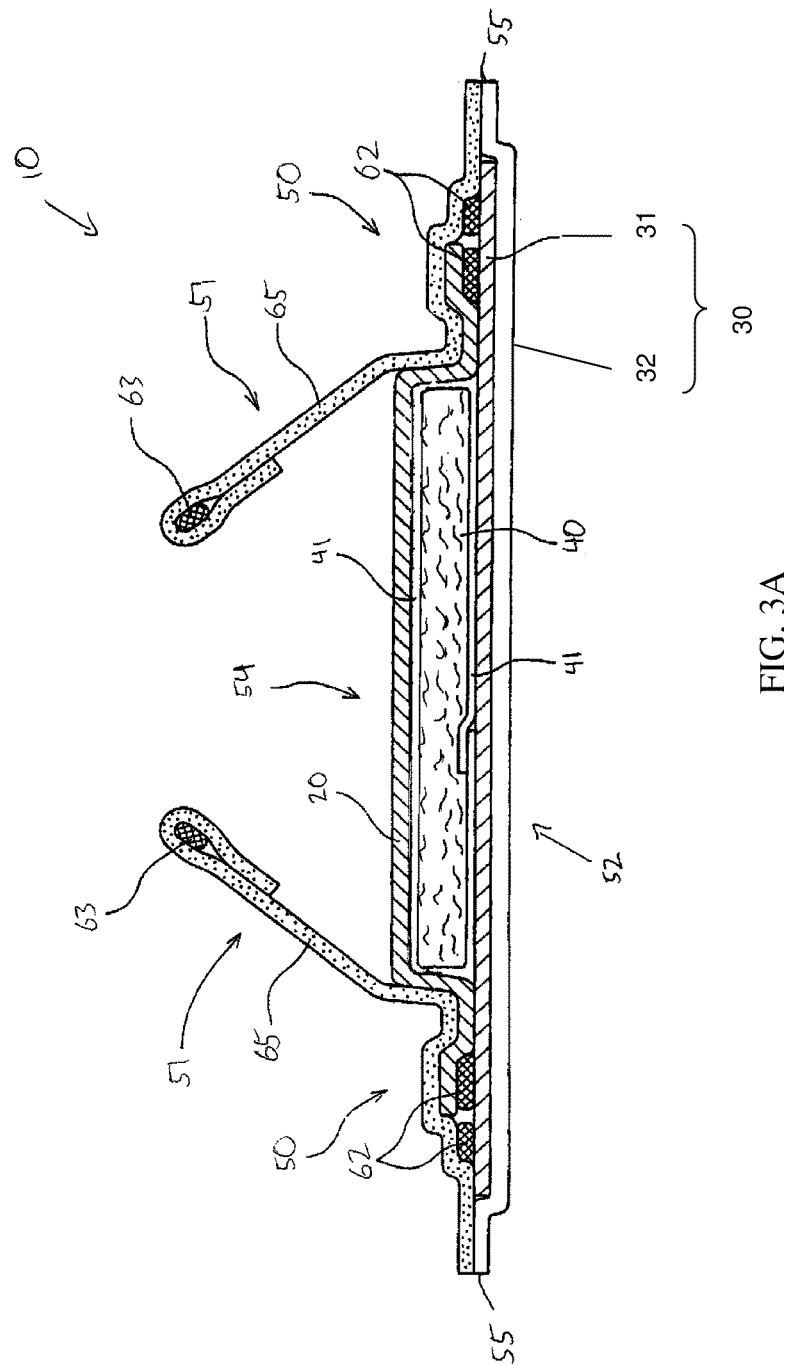
FIG. 3A is a cross-sectional view of an exemplary absorbent article through sectional line 3-3.
Figure 3B:
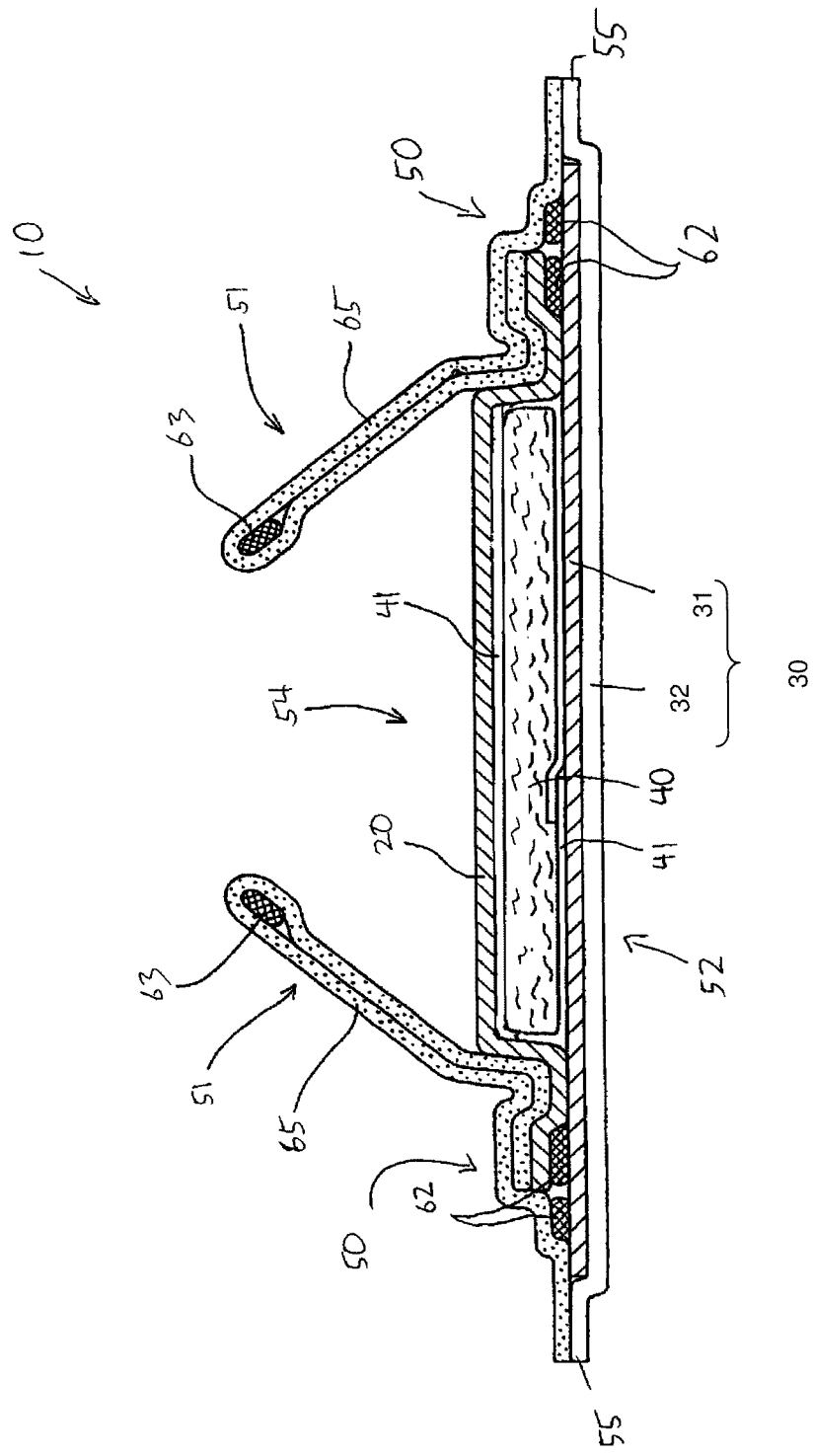
FIG. 3B is a cross-sectional view of an exemplary absorbent article through sectional line 3-3.
Figure 3C:
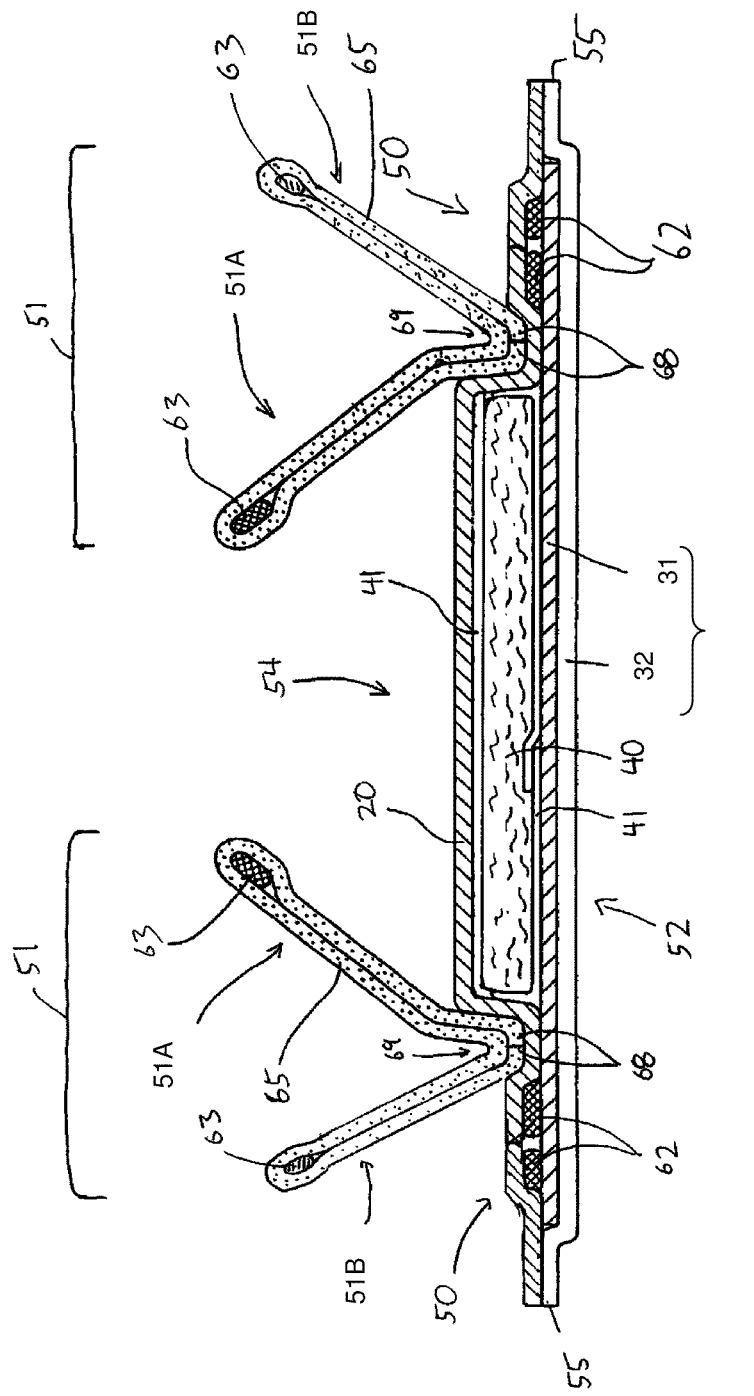
FIG. 3C is a cross-sectional view of an exemplary absorbent article through sectional line 3-3.

FIGS. 3A-C each depict a cross-sectional view of an exemplary cuff configuration along line 3-3 of FIGS. 1 and 2. A gasketing cuff 50 and a barrier cuff 51 are both shown in FIGS. 3A-C, but a single cuff design is equally feasible. FIG. 3A illustrates an exemplary gasketing cuff 50 and barrier cuff 51 configuration. Both cuffs 50 and 51 may share a common substrate 65 along one of their interior and/or exterior surfaces. Barrier cuff 51 is shown in a single layer configuration where a substantial portion of the lateral width the cuff 51 comprises a single ply of the substrate 65. FIG. 3B illustrates an exemplary gasketing cuff 50 and barrier cuff 51 configuration with the barrier cuff 51 in a multiple layer configuration. In the multiple layer configuration, at least two plies of the substrate exist over a substantial portion of the lateral width of the cuff 51. One or more elastic members 62, 63 may be used in each gasketing cuff 50 and/or barrier cuff 51. FIG. 3C illustrates an exemplary dual barrier cuff 51 design having a first barrier cuff 51A and a second barrier cuff 51B. The barrier cuff 51 may include a substrate 65 that forms portions of both the first barrier cuff 51A and the second barrier cuff 51B. The first barrier cuff 51A may be positioned nearer to the longitudinal centerline 59 (shown in FIG. 1) than the second barrier cuff 51B, which may be positioned nearer to the longitudinal edges 55 of the diaper 10. The substrate 65 may envelop an elastic member 63 that may be present in the first barrier cuff 51A and/or the second barrier cuff 51B. Generally, the first barrier cuff 51A and the second barrier cuff 51B contain at least one elastic member 63 enveloped by the substrate 65. The substrate 65 may include two edges 68 joined together at a bond site 69. The edges 68 may be configured in an abutting manner as shown in FIG. 3C; however, other configurations are contemplated herein including configuring the edges 68 in an overlapping manner. In certain embodiments of the dual cuff design, the substrate 65 may be continuous. Dual barrier cuffs 51 made from a continuous or discontinuous substrate 65 are more fully described in U.S. Publication No. 2005/0234411, filed on Apr. 14, 2004, by Ashton, et al. A continuous substrate 65 is shown in FIG. 3C. The substrate 65 forms a continuous path between the opposing edges 68. Along the continuous path, the structure of the first barrier cuff 51A and the second barrier cuff 51B may be formed and the elastic members 63 may be enveloped. The edges 68 may be attached to each other and/or to the diaper 10 at a common bond site 69.

As shown in FIGS. 3A-C, a core cover 41 may be included in certain embodiments of the diaper 10. The core cover 41 may provide structural integrity to the absorbent core assembly 40. The core cover 41 may contain the core 40 components such as cellulosic material and absorbent gelling material, both of which may tend to migrate, move, or become airborne without a physical barrier. The core cover 41 may entirely envelop the absorbent core assembly 40, as shown in FIGS. 3A-B, or may only partially cover the absorbent core assembly 40. The core cover 41 may include a suitable nonwoven, for example, a lightweight nonwoven laminate.

Figure 4:
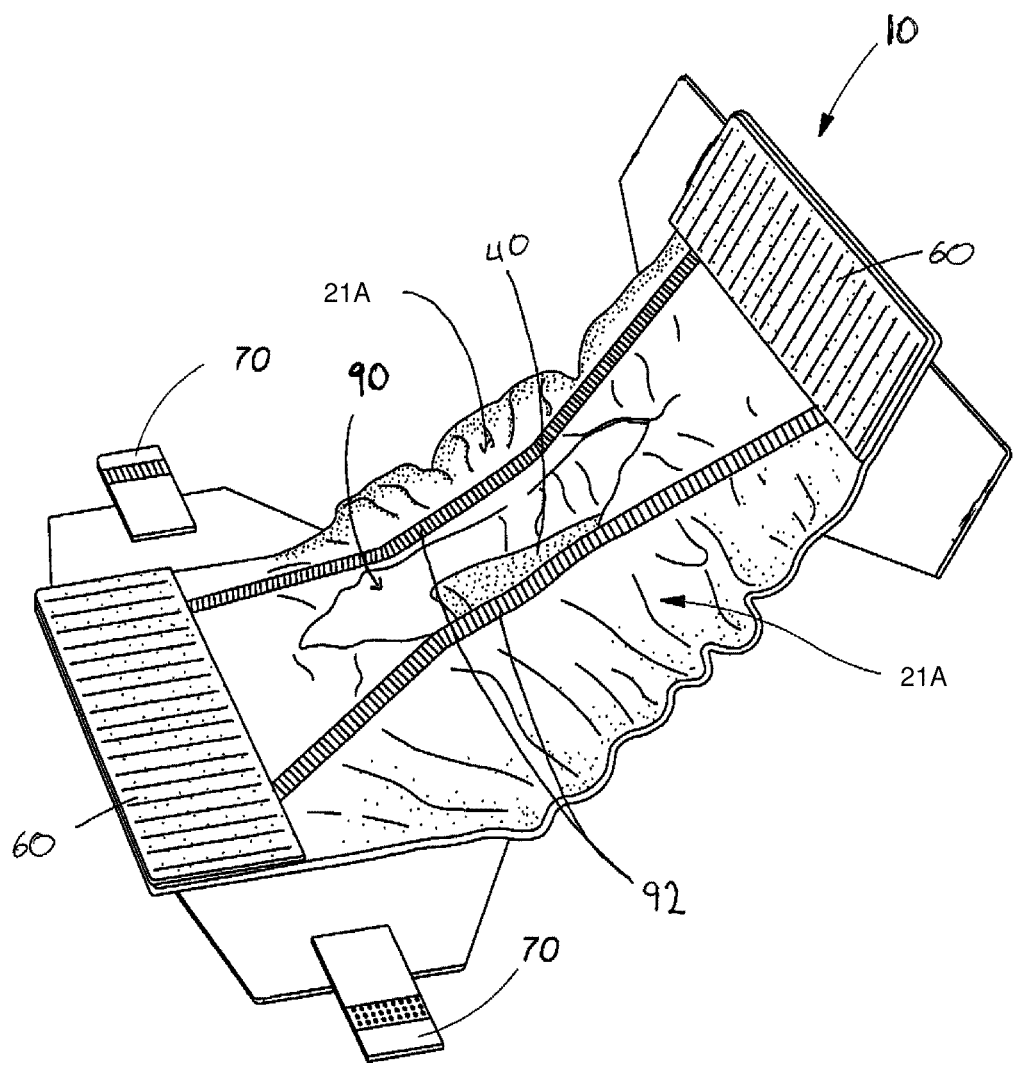
FIG. 4 shows a perspective view of an exemplary absorbent article.

In certain embodiments, the diaper 10 may comprise an elasticized topsheet 20A to provide one or more compartments for receiving and storing body exudates, particularly bowel movements. FIG. 4 shows an exemplary elasticized topsheet 20A. Elasticized topsheets 20A and articles containing them are described in U.S. Pat. No. 6,482,191. FIG. 4 shows the elasticized topsheet 20A with an elongate slit opening 90 and a pair of elastic members 92. The elongate slit opening 90 is provided to allow passage of body exudates into the interior of the diaper 10. The elastic members 92 may provide sufficient tension to the elasticized topsheet 20A so that the topsheet 20A will not sag while in use. While the elasticized topsheet 20A may include any of the material listed above in regard to traditional topsheets, it may be desirable that the elasticized topsheet 20A exhibit some degree of hydrophobicity (e.g., by including a lightweight nonwoven laminate coated with an HSC in the elasticized topsheet 20A). A hydrophobic elasticized topsheet 20A may prevent body exudates stored within the diaper 10 from seeping through the elasticized topsheet 20A and contacting the wearer's skin.

Lightweight Nonwoven Laminate

Figure 5:
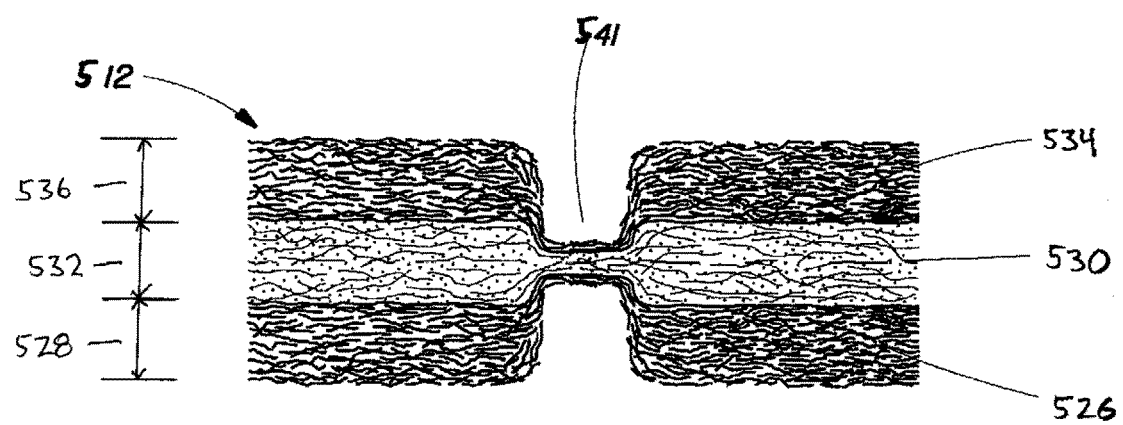
FIG. 5 is a cross-sectional view of an exemplary lightweight, nonwoven laminate.

Nonwoven material and nonwoven laminate formation are well known in the art. Suitable examples of lightweight nonwovens, lightweight nonwoven laminate formation, and processes and equipment for producing such nonwovens and nonwoven laminates are described in U.S. Publication Nos. 2005/0177123 and 2006/0189956. FIG. 5 is a representational, cross-sectional view of a nonwoven laminate 512 showing a first continuous filament layer 528 made of first continuous filaments 526, a fine fiber layer 532 made of fine fibers 530, and a second continuous filament layer 536 made of second continuous filaments 534. A bond 541 may compress the nonwoven laminate 512 and fuse layers together and fibers and/or filaments together. In certain embodiments, the continuous filaments 526 and 534 may have an average fiber diameter in the range of from 12 microns to 30 microns. The basis weight of one or both continuous filament layers 528 and 536 may be varied. In certain embodiments, the basis weight for each continuous filament layer 528, 536 may range from 2 grams per square meter ("gsm") to 20 gsm; from 4 gsm to 10 gsm; or even from 5 gsm to 8 gsm. The first continuous filaments layer 528 and the second continuous filaments layer 536 may have the same basis weight and/or average fiber diameter, but need necessarily do so. The fine fibers 530 may have an average fiber diameter in the range of less than 12 microns or even less than 5 microns. The fine fiber layer 532 may have a basis weight of less than 1.5 gsm; 1.4 gsm; 1.2 gsm; 1.1 gsm; or even less than 1.0 gsm.

The total basis weight for a lightweight nonwoven laminate 512 should not exceed 45 gsm. In certain embodiments, the total basis weight of a lightweight nonwoven laminate material is less than 30 gsm or even 20 gsm. Various basis weight combinations for the individual layers of a laminate are contemplated herein. For example, a suitable combination of basis weights for a first continuous filaments layer 528, a fine fiber layer 532, and a second continuous filaments layer 536 is 6 gsm to 8 gsm; 1.0 gsm; and 6 gsm to 8 gsm, respectively, or even 6 gsm; 3 gsm; 6 gsm, respectively.

Hydrophobic Surface Coating

It may be desirable to incorporate a lightweight nonwoven laminate material into one or more barrier members of an absorbent article. It may further be desirable to include an HSC on at least one surface or surface portion of the lightweight nonwoven laminate material. The HSC may be provided by applying as a non-aqueous, solventless, multicomponent, silicone composition to a surface or surface portion of the material, for example, a composition that includes a reactive vinyl functional siloxane polymer; a solvent free, silicone polymer cross-linker; and a reactive catalyst (e.g., organoplatinum) dispersed in polysiloxane. The HSC composition may be in liquid form during application to a material and/or fiber surface; however, the HSC composition should be substantially free of water or other aqueous media at the time of coating. It is believed, without being limited by theory, that a non-aqueous and solventless HSC composition provides a more uniform distribution of the silicone polymers (i.e., "actives") on the material and/or fiber surface. In certain embodiments, the HSC composition may desirably be hydrophobic to facilitate delivery of the HSC composition to a hydrophobic surface, resulting in a more uniform distribution of the HSC. In certain embodiments, the multicomponent HSC composition may include more than 95% by weight of silicone polymers (i.e., the HSC is composed almost entirely of actives), based on the weight of the HSC composition. Suitable silicone polymers include silicone MQ resins, polydimethysiloxanes, silicone liquid elastomers, and combinations thereof. Suitable polydimethylsilosxanes include vinyl-terminated polydimethsiloxanes, methyl hydrogen dimethylsiloxanes, hydroxyl-terminated polydimethysiloxanes, organo-modified polydimethylsiloxanes, and combinations thereof. In certain embodiments (e.g., when coating a substrate that includes cotton), an HSC that includes fluorinated polymers may be used. Suitable fluorinated polymers include telomers and polymers containing tetrafluoroethylene and/or perfluorinated alkyl chains. For example, fluorinated polymers, which are commercially available from DuPont under the tradename Zonyl® (e.g., Zonyl® 321, 329, 8740, 9027, and 9360) may be suitable.

At least some of the silicone polymers that are present in the HSC composition may be cross-linked after the HSC composition is applied to the surface of a substrate, such as a nonwoven or fiber. The polymers may be cross-linked by any suitable cross-linking process known in the art, for example, during a curing process in which a cross-linking inhibitor from the silicone composition with heat in the presence of a catalyst. During cross-linking, inter-molecular covalent bonds are formed between the silicone polymer molecules. It is believed, without being limited by theory, that the cross-linked molecules may cause the HSC composition, which is typically applied to the substrate in a liquid state, to behave more like a solid (i.e., not exhibit the tendency to flow or migrate, which is typically associated with a liquid). Thus, the cross-linked silicone polymers may help to keep the HSC composition in a desired location. The molecular weight of the silicone polymers prior to cross-linking is typically less than or equal to 4000 MW. After cross-linking, the molecular weight of the cross-linked silicone polymers on the coated surface may be more than 4000 MW; 10,000 MW; 15,000 MW; 20,000 MW; or even more than 25,000 MW. The HSC may be present on the surface of a substrate (e.g., a lightweight nonwoven laminate) in amounts of at least 1 microgram of coating per 1 gram of substrate ("μg/g"). For example, the HSC may be present on the laminate in amounts of at least about 100 μg/g; 200 μg/g; 300 μg/g or even at least 400 μg/g, as determined by a suitable silicon analysis.

The HSC compositions may be delivered to a substrate and/or fiber surface by any means commonly known in the art. One particularly suitable method of delivery is described in copending U.S. Provisional Application Ser. No. 61/156, 150, filed by Tee, et al. on Feb. 27, 2009. Without being limited by theory, it is believed that the HSC compositions disclosed herein, when topically applied to the surface of a fibrous substrate (e.g., nonwoven surface), tend to envelope or at least partially coat one or more fibers and/or fibrous structures of the nonwoven in such a way that a cohesive, uniform film-like network is formed around the fiber and/or fibrous structures, and partially fills the pore network of the nonwoven. This film-like network serves to increase the barrier properties of the component, particularly when exposed to low surface energy fluids. In certain embodiments, HSC compositions may be included as an additive to a hot melt composition (e.g., blended into a thermoplastic melt), which is then formed into fibers and/or a substrate (e.g., by spunbonding, meltblowing, or extruding); however, such embodiments are generally not desirable due to the lack of a suitable film-like network being formed on the fibrous structures. The resulting fibers may exhibit suitable hydrophobic properties, but a nonwoven formed from such fibers may not exhibit the desired barrier properties.

Figure 6:
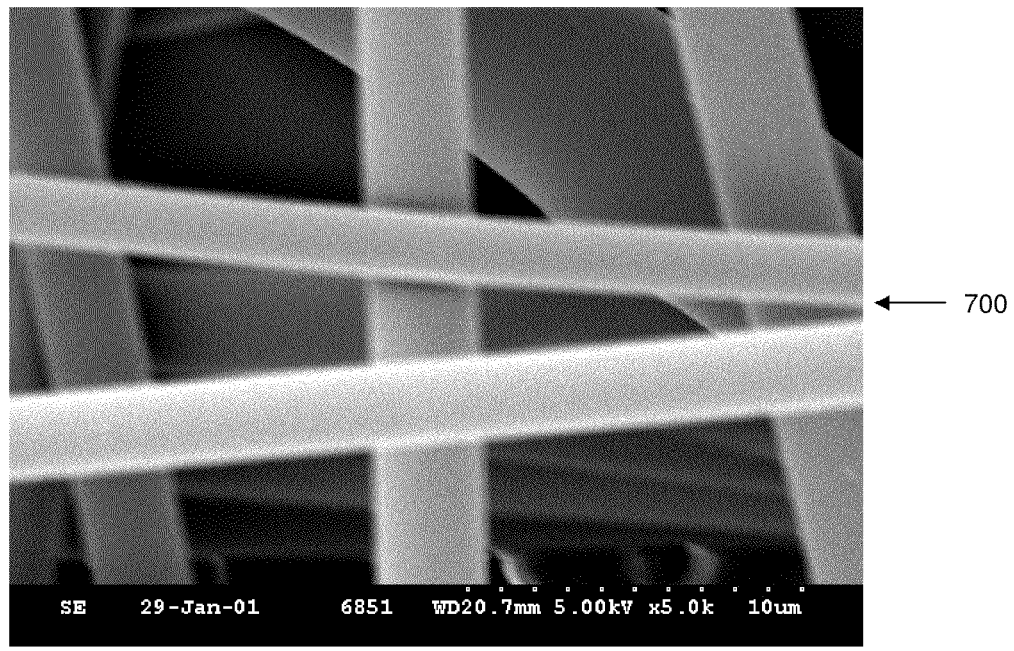
FIG. 6 is a micrograph of a nonwoven.
Figure 7:
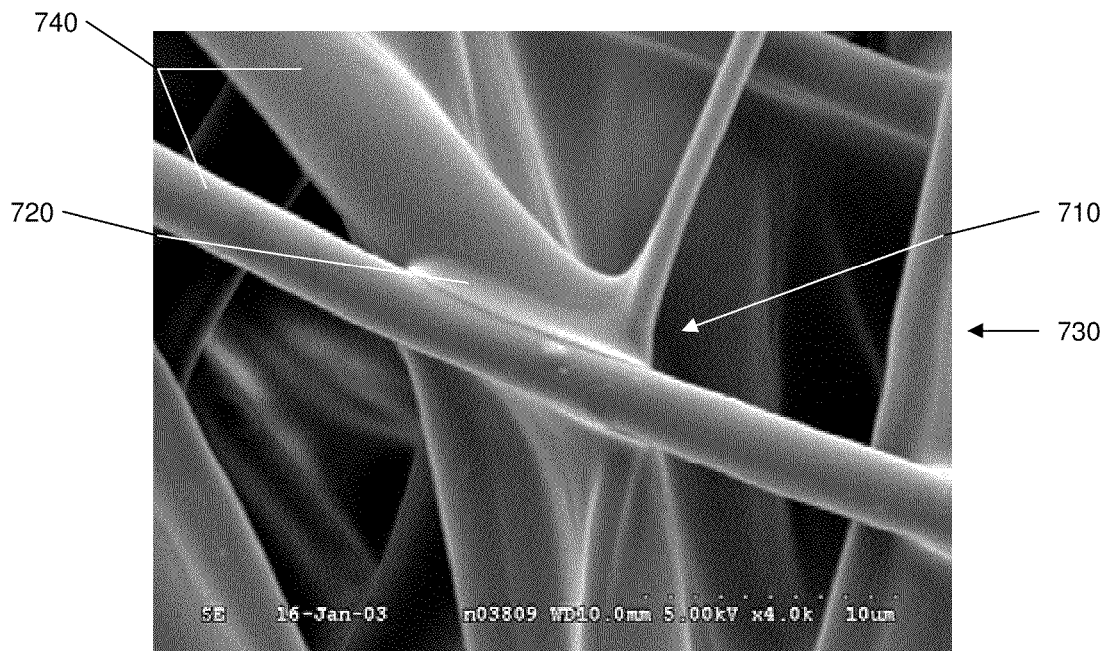
FIG. 7 is a micrograph of a nonwoven treated with a hydrophobic surface coating.

FIG. 6 shows a micrograph of an uncoated 15 gsm meltblown nonwoven 700. In FIG. 7, the nonwoven 700 of FIG. 6 is treated with an HSC 710 to form a coated nonwoven 730, which includes a non-aqueous, solventless, multicomponent, silicone composition. Here, the film-like network 720 is formed between the fibrous structures 740 of the coated nonwoven 730. In certain embodiments, the HSC 710 may be elastomeric. Accordingly, when deposited onto one or more surfaces of an absorbent article component, the HSC 710 may provide at least some elastic properties to the article component when stretched.

It is believed that the HSC composition disclosed herein may provide improved distribution of the actives as compared to an aqueous coating composition that includes a hydrophobic active component (e.g., provides a more uniform HSC). Improved distribution of the actives means that the treated component and/or component portion exhibits improved barrier properties, as evidenced by a higher strike-through time. Suitable strike-through times include strike-through times of greater than 12 seconds, when measured according to the Liquid Strike-through Test described below. For example, strike-through time of between 12 and 20 seconds, 14 and 18 seconds, or even between 15 and 17 seconds. Further, the HSC compositions described herein do not include the additional additives (e.g., surfactants and stablizers) that are typically included in aqueous compositions, and therefore may demonstrate reduced, and ideally no, migration of actives, as compared to conventional coating compositions.

Table 1 below illustrates the strike-through time for a lightweight nonwoven laminate coated with an HSC as disclosed herein. The laminate is a 15 gsm nonwoven available from Polymer Group, Inc., Charlotte, N.C. The nonwoven is a polypropylene, SMS trilaminate configured such that the layers have a basis weight of 7 gsm; 1 gsm; 7 gsm, respectively. The strike-through times are measured on an uncoated sample, a sample coated with an aqueous composition that includes a hydrophobic active component, and an HSC as disclosed herein. The aqueous composition is a 10.4% by weight total actives solution, based on the total weight of the composition. The composition is a mixtures of 25% by weight of SM3200 brand 40% emulsion; 0.5% by weight of SM3010 brand 40% emulsion with catalyst; and 74% water. The SM3200 and SM3010 brand 40% active emulsions are available from Momentive Chemicals. The HSC composition is a 100% active, multicomponent, silicone composition of 92% SylOFF 9110 brand silicone polymer, 5% SylOFF 7682-0000 brand silicone polymer cross-linker and 3% SylOFF 4000 brand catalyst, all available from Dow Corning Corp. The strike-through times are measured according to the Liquid Strike-Through Test described below.

TABLE 1

| 15 gsm PGI nonwoven | Uncoated | Aqueous Composition | HSC Composition |
|---|---|---|---|
| Strikthrough time (s) | 6.61 | 10.92 | 15.96 |

As can be seen from Table 1, an HSC suitable for use herein provides improved strike-through times over the uncoated sample and the sample treated with the aqueous composition.

Test Methods

Silicon Analysis

The amount of elemental silicon coated on a surface is determined by a silicon analysis performed at an external accredited laboratory (e.g., Advanced Testing Laboratory, Cincinnati, Ohio) using compendial methods. HSC coated samples, as described herein, that are submitted for Silicon Analysis primarily include siloxane polymers, which contain elemental silicon, as the hydrophobic active component and nonwoven material, which may be coated or uncoated. Thus, an elemental silicon analysis on the HSC coated nonwoven substrates can detect and quantify the amount of silicone present, which can then be correlated to the amount of HSC present on the coated substrate.

Liquid Strike-Through

The barrier performance of the coated substrates is determined by measuring the time in which a liquid added to the surface of the substrate penetrates the surface of the substrate. The test method conforms to the European Disposables And Nonwovens Association ("EDANA") method No. 150.3-96 using a Lister SN L5725 Model 1998 and an aqueous solution of 0.042% Triton-X-100, which is commercially available through Aldrich Chemicals. The surface tension of the solution should be approximately 30 mN/m-32 mN/m). The test solution is prepared by the following procedure:

Materials Needed: 2.6 g Triton-X-100
    1.0 L Beaker
    6.0 L Erlenmeyer Flask
    1.0 L Graduated Cylinder
    Stir Bar
    Distilled Water
    Analytical Balance (at least 1 kg capacity/2-place)
    Foil Procedure to Prepare 5.0 L:
1. Thoroughly clean and rinse a 6.0 L flask and 1.0 L beaker.
2. Zero the Analytical Balance with doors/lid closed.
3. Place the clean, dry 1.0 L beaker onto the balance, and tare the balance.
4. Using a disposable pipette, carefully add 2.10 g of Triton-X-100 directly to the beaker that is on the balance.

Ensure that as you are adding the Triton-X-100 to the flask, you are not getting it on the neck or sides of the beaker.
5. Using a 1.0 L graduated cylinder, add 998 mL of distilled water to the beaker.
6. Pour the contents of the beaker into the 6.0 L flask.
7. Add 1000 mL of distilled water to the beaker to rinse the Triton-X-100.
8. Pour the distilled water into the 6.0 L flask, combining the contents.
9. Repeat steps 6.-8. three additional times.
10. Place a stir bar into the flask.
11. Cover the flask with foil.
12. Place a Safety Label onto the flask (see example below). Use a piece of masking tape to denote the date of preparation and the initials of the person who prepared the solution.
13. Place the flask of solution onto a stir plate to thoroughly mix (approximately 30 minutes should be sufficient).
14. Measure the surface tension of the solution according to the Interfacial Tension Measurement method below to ensure that it is 32±2 dyne/cm.

Dry Migration Test

This method is used to verify the surface modification of a nonwoven material or test for dry migration of surfactants onto neighboring materials by measuring the dry migration of hydrophilic surfactants from a hydrophilic nonwoven raw material to a hydrophobic nonwoven raw material.

Procedure: Alternating pieces of hydrophobic and hydrophilic nonwovens are placed in a stack in the oven at 60° C. A weight is placed on the stack to maximize physical contact among the nonwovens. The stack plus the weight is left in the oven for 48 hours. After the time, the hydrophobic nonwovens are then analyzed by time-of-flight secondary ion mass spectrometry ("TOF-SIMMS"), which measures the surfactant content that has migrated. TOF-SIMMS can be used as a tool to identify chemical materials on the sample surface and is accomplished by comparison of the mass spectra obtained from the sample to reference spectra obtained from the materials deposited on the sample.

Interfacial Tension Measurement and Contact Angle Measurement

The Interfacial Tension Measurement measures the surface tension of a fluid in units of Dyne per centimeter. This test is performed according to ASTM D-1331, titled "Standard Test Method for Surface and Interfacial Tension of Solutions of Surface Active Agents." The Contact Angle Measurement measures the surface energy of a fluid on a surface. This test is according to ASTM D-7334, titled "Standard Practice for Surface Wettability of Coatings, Substrates and Pigments by Advancing Contact Angle Measurement." Lower advanced contact angle values are indicative of wetting and fluids having lower advanced contact angles tend spread faster on a particular nonwoven material, which may be undesirable, for example, when the material is a barrier material.

Example 1

A multicomponent, silicone, non-aqueous and solventless HSC composition is prepared by mixing a vinyl terminated polydimethyl siloxane, methylhydrogen polydimethyl siloxane and cross-linker and catalyst. The mixture is mixed in a ratio of 92% SylOFF 9110 brand silicone polymer, 5% SylOFF 7682 brand cross-linker and 3% SylOFF 4000 brand catalyst. 400 μg/g of the HSC is deposited on the substrate. Suitable substrates for use in this example include the lightweight nonwoven laminates having a spunbond/meltblown/spunbond laydown in gsm of 6/1/6, 7/1/7, and 8/1/8. The HSC also contains a transition metal catalyst to facilitate the self-cross-linking of the PDMS polymers. The coated substrate is thermally cured at a temperature range of from 80° C. to 120° C. for 0.5-1.0 minute and then stored in a suitable container for later use. After the thermal curing process, the cross-linker is substantially removed from the HSC.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising:
    a. a liquid pervious first topsheet;
    b. an outer cover joined to at least a portion of the topsheet;
    c. an absorbent core disposed between the topsheet and the outer cover;
    d. a barrier member having first and second opposing surfaces, the barrier member including a nonwoven;
    e. a hydrophobic surface coating disposed on at least one surface of the nonwoven such that a coated nonwoven is formed, the hydrophobic surface coating comprising a nonaqueous, solventless, multicomponent silicone composition including at least two silicone polymers and being substantially free of aminosilicones, wherein at least one of the silicone polymers is a vinyl-terminated polydimethylsiloxane, and wherein at least one of the silicone polymers is cross-linked.

2. The article of claim 1, wherein the nonwoven is a lightweight nonwoven laminate material comprising a first continuous filaments layer, a second continuous filaments layer, and a fine fiber layer disposed between the first continuous filaments layer and the second continuous filaments layer, the fine fiber layer having a basis weight of less than 1.5 gsm.

3. The article of claim 1, wherein the nonwoven has a basis weight of less than 40 grams per square meter.

4. The article of claim 1, wherein the barrier member is selected from the group consisting of a core cover, an outer cover, a gasketing cuff, a barrier cuff, an elasticized topsheet, and combinations thereof.

5. The article of claim 1, wherein the nonwoven surface having the hydrophobic surface coating thereon is a skin contacting surface of the barrier member.

6. The article of claim 1, wherein at least one of the silicone polymers is selected from the group consisting of silicone MQ resins, polydimethysiloxanes, epoxy silicones, amido silicones, silicone liquid elastomers, and combinations thereof.

7. The article of claim 1, wherein at least one of the silicone polymers has a molecular weight of at least 4000 MW.

8. The article of claim 1, wherein the hydrophobic surface coating is present in an amount of at least 1 microgram per gram of substrate.

9. The article of claim 1, wherein the coated nonwoven exhibits substantially no migration of actives according to the Dry Migration Test.

10. The article of claim 1, wherein the coated nonwoven has a strike-through time of greater than 12, when measured according to the Liquid Strike-Through Test.

11. An absorbent article comprising:
   a. a liquid pervious first topsheet;
   b. an outer cover at least partially joined to the topsheet;
   c. an absorbent core disposed between the topsheet and the outer cover;
   d. at least one cuff disposed along an outer edge of the article, the cuff having first and second opposing surfaces, the cuff comprising a nonwoven laminate, the nonwoven laminate comprising:
      i. a first continuous filaments layer,
      ii. a second continuous filaments layer,
      iii. a fine fiber layer disposed between the first continuous filaments layer and the second continuous filaments layer and having a basis weight of less than about 1.5 gsm; and
   e. a hydrophobic surface coating comprising a non-aqueous, solventless, multicomponent silicone composition disposed on at least one surface of the cuff, the multicomponent silicone composition comprising at least two silicone polymers and being substantially free of aminosilicones; wherein at least one of the silicone polymers is a vinyl-terminated polydimethylsiloxane; and wherein at least one of the silicone polymers is cross-linked.

12. The article of claim 11, wherein the fine fiber layer has a basis weight of less than about 1.0 gsm.

13. The article of claim 11, wherein the cuff is a barrier cuff comprising a single layer of the nonwoven laminate.

14. The article of claim 11, wherein the cuff is a barrier cuff comprising more than one layer of the nonwoven laminate.

15. The article of claim 11, wherein the cuff is a dual barrier cuff comprising:
   a. a first barrier cuff, and
   b. a second barrier cuff, wherein the second barrier cuff is positioned nearer to a side edge of the article than the first barrier cuff, wherein the first barrier cuff and the second barrier cuff both include the nonwoven laminate.

16. The article of claim 15, wherein the nonwoven laminate is continuous.

17. A disposable substrate article comprising:
   a. a nonwoven substrate; the nonwoven substrate comprising:
      i. a first continuous filaments layer,
      ii. a second continuous filaments layer,
      iii. a fine fiber layer having a basis weight of less than about 1.5 gsm and being disposed between the first continuous filaments layer and the second continuous filaments layer; and
   b. a hydrophobic multicomponent non-aqueous and solventless surface coating disposed on at least one surface of the substrate wherein the coating comprises two or more silicone polymers and wherein the coating is substantially free of aminosilicones; wherein at least one of the silicone polymers is a vinyl-terminated polydimethylsiloxane; and wherein at least one of the silicone polymers is cross-linked.

18. The article of claim 17, wherein the article is selected from the group consisting of disposable garments, wiping cloths, cleaning cloths, shoe covers, packing materials, drapes, and combinations thereof.

* * * * *